United States Patent
Malackowski et al.

(10) Patent No.: US 9,739,674 B2
(45) Date of Patent: Aug. 22, 2017

(54) ISOLATED FORCE/TORQUE SENSOR ASSEMBLY FOR FORCE CONTROLLED ROBOT

(71) Applicant: Stryker Corporation, Kalamazoo, MI (US)

(72) Inventors: Donald W. Malackowski, Schoolcraft, MI (US); Richard T. DeLuca, Kalamazoo, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 14/990,513

(22) Filed: Jan. 7, 2016

(65) Prior Publication Data

US 2016/0202134 A1   Jul. 14, 2016

Related U.S. Application Data

(60) Provisional application No. 62/101,647, filed on Jan. 9, 2015.

(51) Int. Cl.
*G01L 5/22* (2006.01)
*A61B 34/30* (2016.01)
(Continued)

(52) U.S. Cl.
CPC .............. *G01L 5/226* (2013.01); *A61B 34/30* (2016.02); *A61B 34/37* (2016.02); *A61B 34/76* (2016.02);
(Continued)

(58) Field of Classification Search
CPC .............. A61B 34/37; A61B 2090/034; A61B 2090/064; A61B 34/76; A61B 90/03;
(Continued)

(56) References Cited

U.S. PATENT DOCUMENTS

| 5,339,799 A | 8/1994 | Kami et al. |
| 5,408,409 A | 4/1995 | Glassman et al. |

(Continued)

FOREIGN PATENT DOCUMENTS

| FR | 2988320 A1 | 9/2013 |
| WO | WO2013052187 A2 | 4/2013 |

OTHER PUBLICATIONS

English language abstract extracted from espacenet.com database on Jul. 21, 2016, 19 pages. Also see English language equivalent US 2015/0051732.

(Continued)

*Primary Examiner* — Max Noori
(74) *Attorney, Agent, or Firm* — Howard & Howard Attorneys PLLC

(57) ABSTRACT

An isolated force/torque sensor assembly for a force controlled robot includes an end effector for operatively attaching to an arm of the force controlled robot, the end effector having a gripping portion adapted to be gripped by a hand of a user, and a force/torque sensor adapted to be disposed between the gripping portion and the arm of the robot, the force/torque sensor having a high force end effector interface adapted to be attached to the arm of the robot, a low force end effector interface operatively attached to the gripping portion, and a transducer disposed between the high force end effector interface and the low force end effector interface for reacting to loads applied to the low force end effector interface for user controlled positioning of a surgical tool and for generating corresponding output signals, and wherein the transducer is bypassed for high loads.

21 Claims, 3 Drawing Sheets

(51) Int. Cl.
*A61B 34/37* (2016.01)
*A61B 34/00* (2016.01)
*B25J 9/16* (2006.01)
*B25J 1/02* (2006.01)
*B25J 13/08* (2006.01)
*A61B 90/00* (2016.01)

(52) U.S. Cl.
CPC ............... *A61B 90/03* (2016.02); *B25J 1/02* (2013.01); *B25J 9/1633* (2013.01); *B25J 9/1694* (2013.01); *B25J 13/085* (2013.01); *A61B 2034/305* (2016.02); *A61B 2090/034* (2016.02); *A61B 2090/064* (2016.02); *Y10S 901/09* (2013.01)

(58) Field of Classification Search
CPC . G01L 5/226; Y10S 901/09; B25J 1/02; B25J 9/1633; B25J 9/1694; B25J 13/085
USPC ................................. 73/862.05; 700/253, 258
See application file for complete search history.

(56) References Cited

U.S. PATENT DOCUMENTS

| | | | | |
|---|---|---|---|---|
| 8,882,660 B2* | 11/2014 | Phee | ............... | A61B 1/00147 600/139 |
| 8,909,374 B2* | 12/2014 | Fudaba | ............... | B25J 13/02 700/253 |
| 9,002,518 B2* | 4/2015 | Manzo | ............... | A61B 1/00149 700/245 |
| 9,095,984 B2* | 8/2015 | Miyazaki | ............... | B25J 13/085 |
| 2001/0034530 A1* | 10/2001 | Malackowski | ........ | A61B 34/20 606/130 |
| 2007/0156157 A1 | 7/2007 | Nahum et al. | | |
| 2008/0010706 A1 | 1/2008 | Moses et al. | | |
| 2009/0149867 A1 | 6/2009 | Glozman et al. | | |
| 2010/0307265 A1 | 12/2010 | Werthschutzky et al. | | |
| 2011/0112549 A1 | 5/2011 | Neubach et al. | | |
| 2011/0118748 A1 | 5/2011 | Itkowitz | | |
| 2011/0301500 A1 | 12/2011 | Maguire et al. | | |
| 2011/0306985 A1 | 12/2011 | Inoue et al. | | |
| 2012/0209293 A1 | 8/2012 | Carlson et al. | | |
| 2012/0296472 A1* | 11/2012 | Nagai | ............... | B25J 9/1612 700/258 |
| 2013/0030286 A1 | 1/2013 | Alouani et al. | | |
| 2015/0051732 A1 | 2/2015 | Grygorowicz et al. | | |

OTHER PUBLICATIONS

International Search Report for Application No. PCT/US2016/012627 dated Apr. 22, 2016, 11 pages.

* cited by examiner

ISOLATED FORCE/TORQUE SENSOR ASSEMBLY FOR FORCE CONTROLLED ROBOT

CROSS-REFERENCE TO RELATED APPLICATION

The present application claims the benefit of pending U.S. Provisional Patent Application No. 62/101,647, filed Jan. 9, 2015, the entire disclosure of which is hereby incorporated by reference.

TECHNICAL FIELD

The present invention relates generally to a force/torque sensor assembly for a force controlled robot.

BACKGROUND

Medical practitioners have found it useful to use robotic systems to assist in the performance of surgical procedures. Such robotic systems may include a force controlled robot having a moveable arm and an end effector at the end of the arm. Typically, a surgical tool is attached to the end effector. The tool is designed to be applied to a surgical site. Generally, a controller regulates movement of the arm to position the tool with a high degree of accuracy at the surgical site. Optimum control of the force controlled robot is achieved by directly sensing forces applied by a user at a location where the user interacts with the robot. This is typically at the end effector/robot arm interface or part of the end effector itself.

A component of many robotic systems is a force/torque sensor. The force/torque sensor is typically attached between the free end of the arm and the tool. The force/torque sensor monitors forces and torques that are applied to the tool. These may be forces and torques that are applied to the tool as a consequence of the tool pressing against tissue. These also may be forces and torques a user applies in order to set a position and/or orientation of the tool. Signals output by the force/torque sensor are received by the controller. The controller uses these signals to determine a target position for the tool. Based on the determined target position, the controller actuates the arm in order to advance the arm so that the tool is moved to the target position.

In order to ensure all forces and torques applied to the tool are measured, it is common practice to provide a six component force/torque sensor. This type of force/torque sensor measures forces applied to the tool along three axes and torques applied to the tool around the three axes.

One type of six component force/torque sensor is also known as a force/torque transducer. A typical force/torque transducer includes a pair of sensor members, one for attaching to the robot arm and one for attaching to the end effector. A plurality of beams is flexibly mounted between the sensor members and one or more strain gauges are associated with each beam. Each strain gauge generates an electrical signal proportional to a flexure of the beam with which the strain gauge is associated. The output signals from the strain gauges are input variables into an algorithm that yields the measured forces and torques.

One disadvantage of the above force controlled robot is that the force/torque sensor is subjected to all other forces imparted to the tool in addition to the forces presented by the user and these other forces may be in a range that is capable of exceeding the operating range of the force/torque sensor or even high enough to damage the force/torque sensor. This is especially true when the use-case of the force controlled robot is to be a manual positioner for a high impact procedure such as impacting an acetabular cup in a total hip arthroplasty. In this application, the user guides the robot into the correct position to hold the impactor using traditional force control and then manually strikes the tool with a hammer, subjecting the force/torque sensor to the impact forces. Therefore, there is a need in the art to provide a force/torque sensor for a force controlled robot that isolates the force/torque sensor such that the impacting forces are not imparted to the force/torque sensor.

SUMMARY

Accordingly, in one embodiment, the present invention provides an isolated force/torque sensor assembly for a force controlled robot including a gripping portion adapted to be gripped by a hand of a user. The gripping portion is configured to be operatively attached to an arm of the robot. The isolated force/torque sensor assembly also includes a force/torque sensor for disposing between the gripping portion and the arm of the robot. The force/torque sensor has a high force end effector interface for attaching to the arm of the robot, a low force end effector interface operatively attached to the gripping portion, and a transducer disposed between the high force end effector interface and the low force end effector interface for reacting to loads applied to the low force end effector interface for user controlled positioning of a surgical tool and for generating corresponding output signals, and wherein the transducer is bypassed for high loads.

In another embodiment, the present invention provides an isolated force/torque sensor assembly for a force controlled robot including a gripping portion adapted to be gripped by a hand of a user. The gripping portion is configured to be operatively attached to an arm of the robot with a shaft portion extending radially from the gripping portion. A force/torque sensor has a high force end effector interface for attaching to the arm of the robot, a low force end effector interface attached to the shaft portion, and a transducer disposed between the high force end effector interface and the low force end effector interface for reacting to loads applied to said low force end effector interface for generating corresponding output signals.

In another embodiment, the present invention provides an isolated force/torque sensor assembly for a force controlled robot including a gripping portion adapted to be gripped by a hand of a user. The gripping portion is configured to be operatively attached to an arm of the robot. A force/torque sensor has a high force end effector interface for attaching to the arm of the robot and a low force end effector interface attached to one end of the gripping portion. The gripping portion floats with the low force end effector interface. The force/torque sensor also includes a transducer disposed between the high force end effector interface and the low force end effector interface for reacting to loads applied to the low force end effector interface for generating corresponding output signals.

In another embodiment, the present invention provides an isolated force/torque sensor assembly for a force controlled robot including a gripping portion adapted to be gripped by a hand of a user. The gripping portion is configured to be operatively attached to an arm of the robot with a shaft portion extending from the gripping portion. A force/torque sensor has a high force end effector interface for attaching to the arm of the robot, a low force end effector interface attached to the shaft portion, a plurality of beams extending between the low force end effector interface and the high force end effector interface, and a transducer disposed between the high force end effector interface and the low force end effector interface for reacting to loads applied to the low force end effector interface for generating corresponding output signals.

Other features and advantages of the present invention will be readily appreciated, as the same becomes better understood, after reading the subsequent description taken in conjunction with the accompanying drawings.

DETAILED DESCRIPTION

Figure 1:
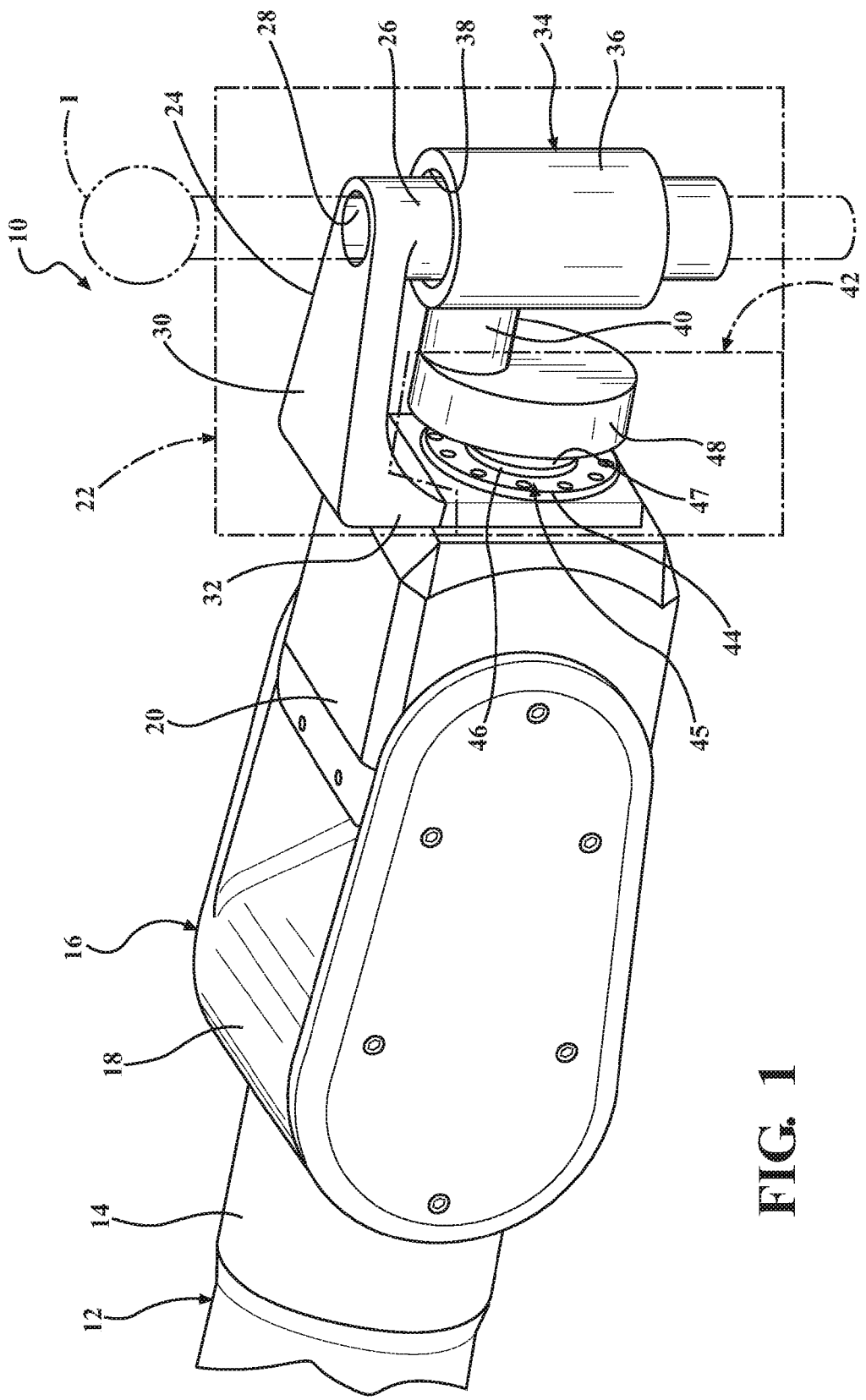
FIG. 1 is a perspective view of one embodiment of an isolated force/torque sensor assembly, according to the present invention, illustrated in operational relationship with a force controlled robot.

Referring to the drawings and in particular FIG. 1, one embodiment of an isolated torque/force sensor assembly 10, according to the present invention, is shown in operational relationship with a robot, generally indicated at 12. In one embodiment, the robot 12 is of a force controlled type and includes a robot arm 14 extending from a body (not shown) of the robot 12. The robot 12 also includes a wrist joint, generally indicated at 16, attached to an end of the robot arm 14. In this embodiment, the wrist joint 16 includes a bracket 18 attached to the robot arm 14. The bracket 18 is generally "U" shaped. The wrist joint 16 also includes a flange 20 pivotally connected to the bracket 18. The flange 20 is generally rectangular in shape, but may be any suitable shape. The flange 20 is disposed in the opening of the bracket 18 and pivotally connected to the bracket 18 by a suitable mechanism such as a pin (not shown). It should be appreciated that the flange 20 pivots or rotates relative to the bracket 18. It should also be appreciated that the flange 20 is controlled by an actuator (not shown) such as an encoder, motor, and gearbox that is grounded to the bracket 18 to pivot the flange 20.

In one embodiment, the robot 12 further includes an end effector, generally indicated at 22 in the dashed lines, mounted to the wrist joint 16. The end effector 22 includes a tool holder or guide 24. The guide 24 includes a guide portion 26 extending axially. The guide portion 26 is generally cylindrical in shape. The guide portion 26 includes an aperture 28 extending axially therethrough to allow a tool such as a reamer or impacter (I) to extend therethrough. The guide 24 also includes a support portion 30 extending radially from the guide portion 26. In one embodiment, the support portion 30 extends from an upper end of the guide portion 26. The guide 24 further includes a mounting portion 32 extending from the support portion 30 for attachment to the flange 20 of the wrist joint 16. The mounting portion 32 may be mounted to the flange 20 by a suitable mechanism such as fasteners (not shown). The guide 24 is integral, unitary, and/or one-piece to form a single rigid body. It should be appreciated that the guide 24 is used by a user (not shown) to insert the tool such as the reamer or impacter during hip replacement surgery.

As illustrated in FIG. 1, the isolated force/torque sensor assembly 10 includes a user interface, generally indicated at 34, operatively cooperating with the guide 24. In one embodiment, the user interface 34 includes a gripping portion 36 extending axially to allow a hand of the user to grip the user interface 34. The gripping portion 36 is generally cylindrical in shape. The gripping portion 36 includes an aperture 38 extending axially therethrough to allow the guide portion 26 of the guide 24 to extend therethrough. The user interface 34 may also include a shaft portion 40 extending radially from the gripping portion 36. The user interface 34 is integral, unitary, and/or one-piece to form a single rigid body. It should be appreciated that the gripping portion 36 has one hundred percent clearance around the guide portion 26 of the guide 24. It should also be appreciated that the user interface 34 is shaped for being gripped by a hand of the user.

Referring to FIG. 1, the isolated force/torque sensor assembly 10 includes a force/torque sensor, generally indicated at 42 in phantom lines. As illustrated, the force/torque sensor 42 is provided to react to loads applied to the user interface 34. The loads include forces and torques applied to the user interface 34 by a user when the user desires to set a position and/or orientation of the guide 24. It should be appreciated that a robot controller (not shown) sets the position of the robot arm 14 and wrist joint 16, and thus the guide 24, based on the forces and torques measured by the force/torque sensor 42.

As illustrated in FIG. 1, the force/torque sensor 42 acts between the robot arm 14 and the user interface 34. The force/torque sensor 42 includes a high force end effector interface 44, a transducer 45, and a low force end effector interface 48. The interfaces 44 and 48 support the force/torque sensor 42 for operation between the robot arm 14 and the user interface 34. The high force end effector interface 44 may either be part of the guide 24 or end effector 22. The low force end effector interface 48 may be part of the user interface 34. It should be appreciated that the force/torque sensor 42 is of a six axis force transducer type. It should also be appreciated that the high force end effector interface 44 may be connected to or integral with the mounting portion 32 of the guide 24.

As illustrated in FIG. 1, the high force end effector interface 44 is a plate mounted to the flange 20 of the robot 12 by a suitable mechanism such as fasteners (not shown). The low force end effector interface 48 is mounted to or integral with the user interface 34. The transducer 45 is disposed between the interfaces 44 and 48.

The transducer 45 includes a first sensor member 46 such as a first sensor plate fixed to the high force end effector interface 44 by a suitable mechanism such as fasteners (not shown). The transducer 44 also includes a second sensor member 47 such as a second sensor plate fixed to the low force end effector interface 48 by a suitable mechanism such as fasteners (not shown). A plurality of beams (not shown) is flexibly mounted between the first sensor member 46 and second sensor member 47. One or more strain gauges (not shown) are associated with each beam. Each strain gauge generates an electrical signal proportional to a flexure of the beam with which the strain gauge is associated. The transducer 45 may be of a silicon strain gauge type. Such a transducer 45 is commercially available from ATI Industrial Automation of Apex, N.C. The transducer 45 is connected by cabling to a force/torque controller (not shown) or the robot controller.

It should be appreciated that the high force end effector interface 44 is mechanically grounded to the robot arm 14, bypassing the transducer 45 of the force/torque sensor 42 when any forces and/or torque are applied to the guide 24. It should also be appreciated that the low force end effector interface 48 is mechanically attached to the force/torque sensor 42 for fine motion control. It should be appreciated that the first sensor member 46 may be integrated into the high force end effector interface 44 and the second sensor member 47 may be integrated into the low force end effector interface. It should still further be appreciated that the force/torque sensor 42 may be integrated into the robot 12 and not the end effector 22.

In addition, the isolated force/torque sensor assembly 10 may include a second force/torque sensor (not shown) placed on the guide 24 to measure the other forces and added to the hand force of the first force/torque sensor 42 to compute total force. In the same way, the second force/torque sensor could be placed directly at the end of the flange 20 to measure total force and be able to compute a tool force by subtracting hand force of the first force/torque sensor 42 from the total force.

The isolated force/torque sensor assembly 10 is considered to be in a loaded state when loads are applied to the user interface 34. When loads (e.g., forces and/or torques) are applied to the isolated force/torque sensor assembly 10, the interfaces 44 and 48 can engage in six types of displacement relative to each other. Three of the movements are translation, along the x-axis, arbitrarily, the horizontal axis through the interfaces 44 and 48, along the y-axis, arbitrarily the vertical axis through the interfaces 44 and 48, and along the z-axis, arbitrarily the axis through the center of the interfaces 44 and 48 that extends in and out of the plane of FIG. 1. The low force end effector interface 48 can also engage in at least some rotational movement around each of the above-identified axes. Typically as a result of the application of forces and torques to the isolated force/torque sensor assembly 10, the low force end effector interface 48 engages in several of these movements.

In one application, a user (not shown) may dispose a reamer (not shown) through the aperture 28 of the guide portion 26 of the guide 24 to ream out bone (not shown) of a hip socket (not shown) of a patient (not shown) for an acetabular cup implant (not shown). Once completed, the user may place the acetabular cup implant in the hip socket. The user may then dispose a tool such as an impactor (I) through the aperture 28 of the guide portion 26 of the guide 24 and hit the impacter (I) with a hammer (not shown). The user may then use the robot 12 in a vibration mode to set the acetabular cup implant in place. When hitting the impactor (I) with the hammer, high forces may be imparted to the guide 24. These high forces are grounded by virtue of the high force end effector interface 44. These forces also bypass the transducer 45 owing to the clearance between the guide portion 26 and the gripping portion 36.

Figure 2:
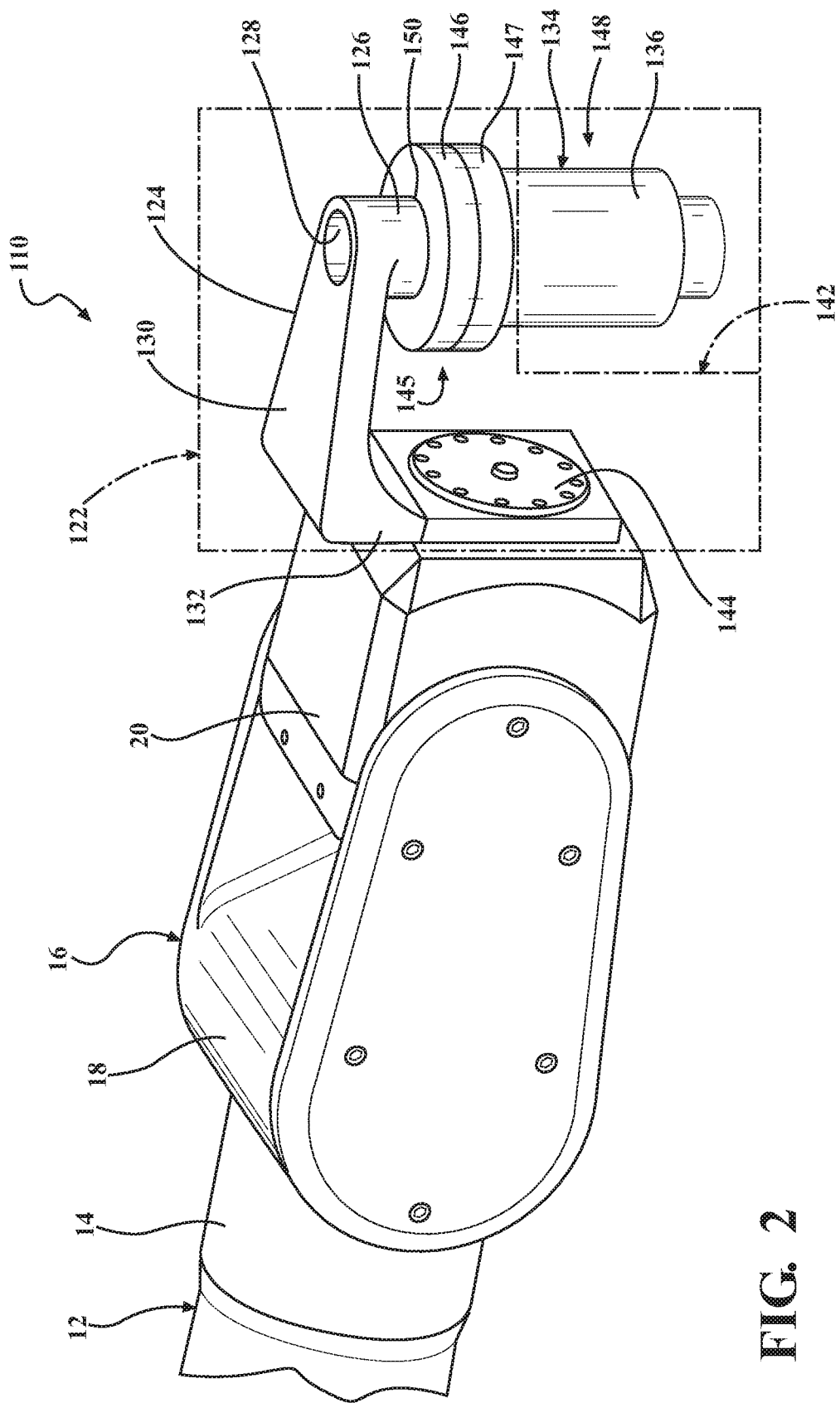
FIG. 2 is a perspective view of another embodiment of an isolated force/torque sensor assembly, according to the present invention, illustrated in operational relationship with a force controlled robot.

Referring to FIG. 2, another embodiment, according to the present invention, of the isolated force/torque sensor assembly 10 is shown. Like parts of the isolated force/torque sensor assembly 10 have like reference numerals increased by one hundred (100). In this embodiment, the isolated force/torque sensor assembly 110 includes the force/torque sensor 142 integrated into the user interface 134. The end effector 122 includes the guide 124 having the guide portion 126 with the aperture 128, support portion 130, and mounting portion 132. The user interface 134 includes the gripping portion 136 disposed about the guide portion 126 of the guide 124. There is one hundred percent (100%) clearance between the guide portion 126 and the gripping portion 136. The force/torque sensor 142 includes the high force end effector interface 144, transducer 145, and the low force end effector interface 148. In this embodiment, the guide 124 is part of the high force end effector interface 144 mounted to the flange 20 and the low force end effector interface 148 is at an end of the gripping portion 136. The transducer 145 is generally circular in shape and has an aperture 150 extending therethrough to allow the guide portion 126 of the guide 124 to extend therethrough. The transducer 145 includes a first sensor member 146 such as a first sensor plate fixed to the guide portion 126 by a suitable mechanism and a second sensor member 147 such as a second sensor plate fixed to the gripping portion 136 by a suitable mechanism. A plurality of beams (not shown) is flexibly mounted between the first sensor member 146 and second sensor member 147. One or more strain gauges (not shown) are associated with each beam. Each strain gauge generates an electrical signal proportional to a flexure of the beam with which the strain gauge is associated. The low force end effector interface 148 of the force/torque sensor 142 is disposed about the guide portion 126 of the guide 124. The transducer 145 is connected by cabling to a force/torque controller (not shown) or the robot controller. It should be appreciated that the high force end effector interface 144 is mechanically grounded to the robot arm 14, bypassing the transducer 145 of the force/torque sensor 142 when any forces and/or torque are applied to the guide 124. It should be appreciated that the gripping portion 136 floats about the guide portion 126 when connected to the transducer 145 of the force/torque sensor 142.

It should be appreciated that the high force end effector interface 144 is mechanically grounded to the robot arm 14. It should also be appreciated that the low force end effector interface 148 is mechanically fixed to the gripping portion 136 and is connected by the transducer 145 to the high force end effector interface 144 for fine motion control. It should further be appreciated that the operation of the isolated force/torque sensor assembly 110 is similar to the isolated force/torque sensor assembly 10.

Figure 3:
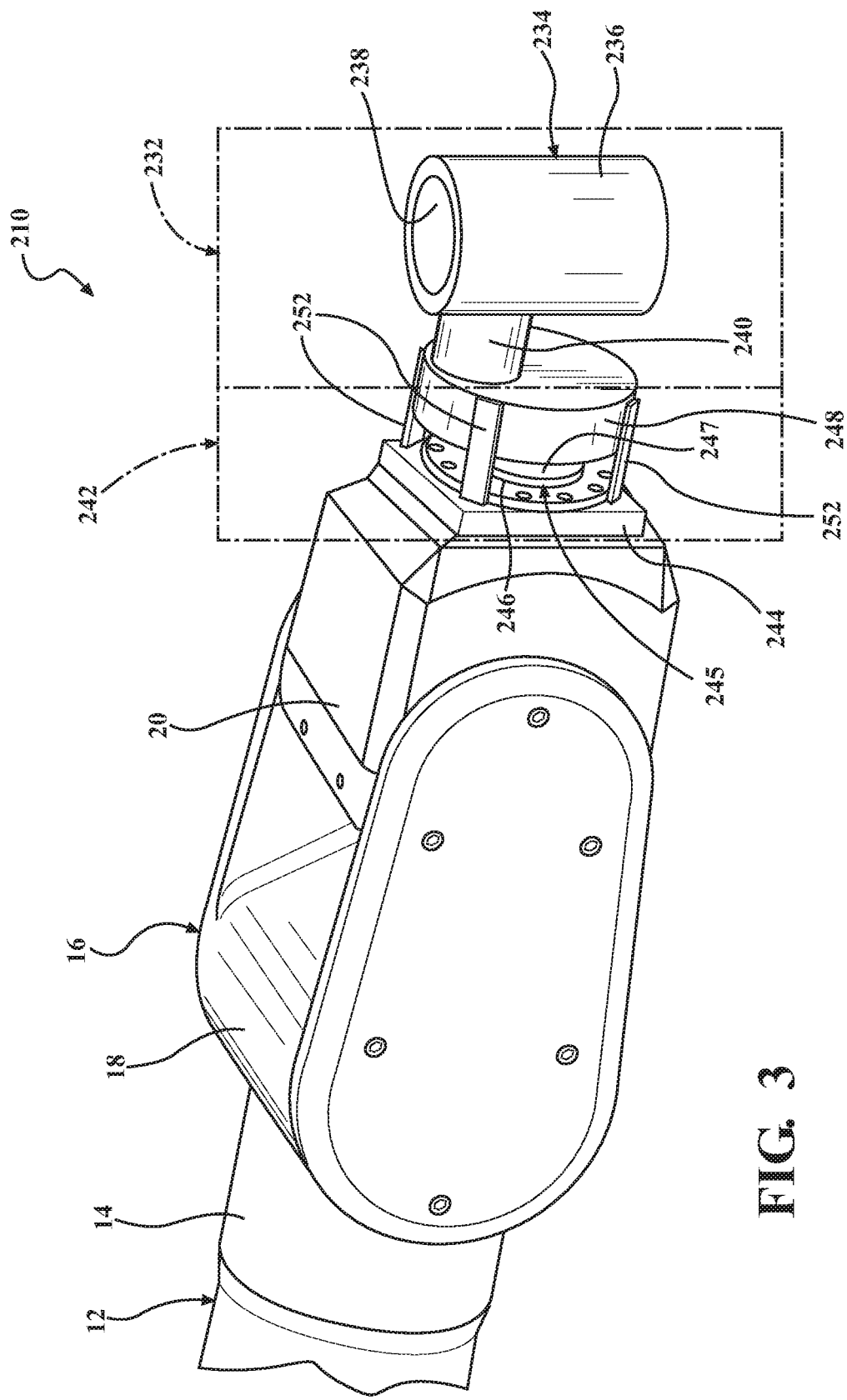
FIG. 3 is a perspective view of yet another embodiment of an isolated force/torque sensor assembly, according to the present invention, illustrated in operational relationship with a force controlled robot.

Referring to FIG. 3, yet another embodiment, according to the present invention, of the isolated force/torque sensor assembly 10 is shown. Like parts of the isolated force/torque sensor assembly 10 have like reference numerals increased by two hundred (200). In this embodiment, the isolated force/torque sensor assembly 210 includes the user interface 234 bridged across the force/torque sensor 242. In one embodiment, the user interface 234 includes a gripping portion 236 extending axially to allow a hand of the user to grip the user interface 234. The gripping portion 236 is generally cylindrical in shape. The gripping portion 236 includes an aperture 238 extending axially therethrough for receiving tools such as the reamer or impactor (I). The user interface 234 may also include a shaft portion 240 extending radially from the gripping portion 236. The user interface 234 is integral, unitary, and/or one-piece to form a single rigid body. It should be appreciated that, in this embodiment, the end effector 232 may be solely the user interface 234 or the user interface 234 and force/torque sensor 242 combined.

As illustrated in FIG. 3, the force/torque sensor 242 includes a high force end effector interface 244, a transducer 245, and a low force end effector interface 248. The low force end effector interface 248 has attachments such as flexible beams 252 for high force use that bridge across the sensitive transducer 245 that increase the overload capacity of the isolated force/torque sensor assembly 210, but still allow the force/torque signal to be generated. The beams 252 are generally rectangular in shape, but may be any suitable shape. The beams 252 are disposed circumferentially about the low force end effector interface 248 and have one end connected by a suitable mechanism such as welding to the low force end effector interface 248.

The beams 252 have another end spaced a predetermined distance from the high force end effector interface 244. The beams 252 may be machined or otherwise arranged to contact the high force end effector interface 244 upon application of larger loads to prevent overload of the transducer 245. The beams 252 may be calibrated so that the beams 252 contact the high force end effector interface 244 at a predetermined load. Thus, the beams 252 may act as stops to contact the high force end effector interface 244 when larger loads, such as the predetermined load, are applied to the user interface 232. In one embodiment, strain gauges 246 may be disposed on the beams 252. Thus, force and/or torque measurements could continue to be made once the beams 252 contact the high force end effector interface 244 albeit at a lower sensitivity/resolution. It should further be appreciated that the operation of the isolated force/torque sensor assembly 210 is similar to the isolated force/torque sensor assembly 10.

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

What is claimed is:

1. An isolated force/torque sensor assembly for a force controlled robot comprising:
   a gripping portion adapted to be gripped by a hand of a user and configured to be operatively attached to an arm of the force controlled robot; and
   a force/torque sensor for disposing between said gripping portion and the arm of the robot, said force/torque sensor having a high force end effector interface for attaching to the arm of the robot, a low force end effector interface operatively attached to said gripping portion, and a transducer disposed between said high force end effector interface and said low force end effector interface for reacting to loads applied to said low force end effector interface for user controlled positioning of a surgical tool and for generating corresponding output signals, and wherein said transducer is bypassed for high loads.

2. An isolated force/torque sensor assembly as set forth in claim 1 wherein said gripping portion is generally cylindrical in shape.

3. An isolated force/torque sensor assembly as set forth in claim 1 wherein said low force end effector interface is attached to one end of said gripping portion.

4. An isolated force/torque sensor assembly as set forth in claim 1 including a shaft portion extending from said gripping portion and attached to said low force end effector interface.

5. An isolated force/torque sensor assembly as set forth in claim 4 wherein said gripping portion, said shaft portion, and said low force end effector interface are integral and one-piece.

6. An isolated force/torque sensor assembly as set forth in claim 1 wherein said high force end effector interface is adapted to be mechanically grounded to the arm of the robot.

7. An isolated force/torque sensor assembly as set forth in claim 1 including a plurality of beams extending between said low force end effector interface and said high force end effector interface.

8. An isolated force/torque sensor assembly as set forth in claim 7 wherein said beams are flexible.

9. An isolated force/torque sensor assembly as set forth in claim 1 wherein said gripping portion floats with said low force end effector interface.

10. An isolated force/torque sensor assembly for a force controlled robot comprising:
    a gripping portion adapted to be gripped by a hand of a user and configured to be operatively attached to an arm of the force controlled robot;
    a shaft portion extending radially from said gripping portion; and
    a force/torque sensor having a high force end effector interface adapted to be attached to the arm of the robot, a low force end effector interface attached to said shaft portion, and a transducer disposed between said high force end effector interface and said low force end effector interface for reacting to loads applied to said low force end effector interface for generating corresponding output signals.

11. An isolated force/torque sensor assembly as set forth in claim 10 wherein said gripping portion is generally cylindrical in shape.

12. An isolated force/torque sensor assembly as set forth in claim 10 wherein said gripping portion, said shaft portion, and said low force end effector interface are integral and one-piece.

13. An isolated force/torque sensor assembly as set forth in claim 10 wherein said high force end effector interface is adapted to be mechanically grounded to the arm of the robot.

14. An isolated force/torque sensor assembly for a force controlled robot comprising:
    a gripping portion adapted to be gripped by a hand of a user and configured to be operatively attached to an arm of the force controlled robot; and
    a force/torque sensor having a high force end effector interface adapted to be attached to the arm of the robot, said high force end effector interface having a guide extending through said gripping portion, a low force end effector interface attached to one end of said gripping portion, said gripping portion floating with said low force end effector interface, and a transducer disposed between said high force end effector interface and said low force end effector interface for reacting to loads applied to said low force end effector interface for generating corresponding output signals.

15. An isolated force/torque sensor assembly as set forth in claim 14 wherein said gripping portion is generally cylindrical in shape.

16. An isolated force/torque sensor assembly as set forth in claim 14 wherein said high force end effector interface is adapted to be mechanically grounded to the arm of the robot.

17. An isolated force/torque sensor assembly for a force controlled robot comprising:
    a gripping portion adapted to be gripped by a hand of a user and configured to be operatively attached to an arm of the force controlled robot;
    a shaft portion extending from said gripping portion; and
    a force/torque sensor having a high force end effector interface adapted to be attached to the arm of the robot, a low force end effector interface attached to said shaft portion, a plurality of beams extending between said low force end effector interface and said high force end effector interface and spaced from said high force end effector interface to act as stops against said high force end effector interface in response to excessive force on said force/torque sensor, and a transducer disposed between said high force end effector interface and said low force end effector interface for reacting to loads applied to said low force end effector interface for generating corresponding output signals.

18. An isolated force/torque sensor assembly as set forth in claim 17 wherein said gripping portion is generally cylindrical in shape.

19. An isolated force/torque sensor assembly as set forth in claim 17 wherein said gripping portion, said shaft portion, and said low force end effector interface are integral and one-piece.

20. An isolated force/torque sensor assembly as set forth in claim 17 wherein said high force end effector interface is adapted to be mechanically grounded to the arm of the robot.

21. An isolated force/torque sensor assembly as set forth in claim 17 wherein said beams are flexible.

\* \* \* \* \*